US011026839B2

(12) United States Patent
Daphna et al.

(10) Patent No.: US 11,026,839 B2
(45) Date of Patent: Jun. 8, 2021

(54) TREATMENT TO IMPROVE ADHESIVE PROPERTIES OF CORNEAL IMPLANT

(71) Applicant: EyeYon Medical Ltd., Nes Ziona (IL)

(72) Inventors: Ofer Daphna, Beit Elazari (IL); Nahum Ferera, Petah Tikva (IL); Dmitry Dubson, Rehovot (IL)

(73) Assignee: EyeYon Medical Ltd., Nes Ziona (IL)

( * ) Notice: Subject to any disclaimer, the term of this patent is extended or adjusted under 35 U.S.C. 154(b) by 0 days.

(21) Appl. No.: 17/147,486

(22) Filed: Jan. 13, 2021

(65) Prior Publication Data

US 2021/0128359 A1 May 6, 2021

Related U.S. Application Data

(63) Continuation of application No. 15/864,250, filed on Jan. 8, 2018.

(51) Int. Cl.
| | | |
|---|---|---|
| *A61F 2/14* | (2006.01) | |
| *B29C 71/00* | (2006.01) | |
| *A61F 9/008* | (2006.01) | |
| *A61F 2/00* | (2006.01) | |
| *B23K 26/352* | (2014.01) | |

(Continued)

(52) U.S. Cl.
CPC ........ *A61F 9/00825* (2013.01); *A61F 2/0077* (2013.01); *A61F 2/142* (2013.01); *A61F 2/145* (2013.01); *A61F 2/1451* (2015.04); *A61F 2002/0081* (2013.01); *A61F 2009/00853* (2013.01); *A61F 2009/00872* (2013.01); *A61F 2240/001* (2013.01); *B23K 26/352* (2015.10); *B23K 2103/42* (2018.08);

(Continued)

(58) Field of Classification Search
None
See application file for complete search history.

(56) References Cited

U.S. PATENT DOCUMENTS 5,104,590 A 4/1992 Blake
5,152,759 A * 10/1992 Parel ................... A61F 9/008
606/17

(Continued)

FOREIGN PATENT DOCUMENTS

CA 2752046 8/2010
WO 2004/024035 3/2004

(Continued)

OTHER PUBLICATIONS

Jay L, Bourget J-M, Goyer B, Singh K, Brunette I, Ozaki T, et al. (2015) Characterization of Tissue-Engineered Posterior Corneas Using Secondand Third-Harmonic Generation Microscopy. PLoS ONE 10(4): (Year: 2015).*

(Continued)

*Primary Examiner* — Cachet I Proctor
(74) *Attorney, Agent, or Firm* — Dekel Patent Ltd.; David Klein

(57) ABSTRACT

A method is described of improving adhesion of an ocular implant to corneal tissue by forming an implant adhesive layer on the ocular implant, the implant adhesive layer having greater adhesive strength than a rest of the implant or by forming a corneal adhesive layer on a posterior surface of a posterior portion of the corneal tissue, the corneal adhesive layer having greater adhesive strength than a rest of the corneal tissue.

26 Claims, 1 Drawing Sheet

(51) Int. Cl.
  *B23K 103/00* (2006.01)
  *B29C 71/02* (2006.01)
  *B29C 71/04* (2006.01)
  *B29L 31/00* (2006.01)
(52) U.S. Cl.
  CPC .............. *B29C 71/02* (2013.01); *B29C 71/04* (2013.01); *B29L 2031/7532* (2013.01)

(56) References Cited

U.S. PATENT DOCUMENTS

| | | | |
|---|---|---|---|
| 2002/0006394 A1* | 1/2002 | Redmond | A61F 9/008 424/93.7 |
| 2002/0022606 A1* | 2/2002 | Kochevar | A61P 27/02 514/81 |
| 2007/0182920 A1 | 8/2007 | Back | |
| 2011/0208300 A1* | 8/2011 | de Juan, Jr. | A61F 2/142 623/5.14 |
| 2012/0150160 A1* | 6/2012 | Vogler | A61F 9/008 606/4 |

FOREIGN PATENT DOCUMENTS

| | | |
|---|---|---|
| WO | 2009/145842 | 12/2009 |
| WO | 2009/146151 | 12/2009 |

OTHER PUBLICATIONS

Raiu et al. Surface Modification of PMMA to Improve Adhesion to Corneal Substitutes in a Synthetic Core-Skirt Keratoprosthesis. ACS Applied Materials and Interfaces. 7. pp. 21690-21702 (2015) (Year: 2015).*
PCT Search Report and Written Opinion PCT/IB2019/050046, dated May 8, 2019.
U.S. Appl. No. 15/864,250, Office Action, dated Feb. 20, 2020, parent application, and references cited therein.
U.S. Appl. No. 15/864,250, Office Action, dated Aug. 24, 2020, parent application, and references cited therein.

* cited by examiner

TREATMENT TO IMPROVE ADHESIVE PROPERTIES OF CORNEAL IMPLANT

CROSS-REFERENCE TO OTHER APPLICATIONS

This application claims priority from U.S. patent application Ser. No. 15/864,250, filed Jan. 8, 2018, which is incorporated herein by reference.

FIELD OF THE INVENTION

The present invention relates generally to corneal implants, such as for treating an over-hydrated, edematous cornea, and particularly to creating an adhesive layer on the implant and/or the corneal tissue to improve adhesion of the implant to the corneal tissue.

BACKGROUND OF THE INVENTION

U.S. Pat. Nos. 8,109,997 and 8,500,803 to Daphna describe bonding a hydrophobic pseudo-endothelial implant to a posterior portion of the cornea adjacent the aqueous humor with a binding agent. The implant serves as a water barrier enabling dehydration of the cornea, and may be used in the treatment of an edematous cornea.

The adhesion of an implant to corneal tissue without sutures or mechanical fasteners poses a challenge. The adhesive materials must be compatible with the ocular environment and yet must provide good adhesion for a long time without degradation in the ocular quality of the eye.

SUMMARY OF THE INVENTION

The present invention relates to methods of treating a surface to create an adhesive layer on a corneal implant and/or corneal tissue to improve adhesion of the implant to the corneal tissue, as is described more in detail hereinbelow.

The invention prepares the surface of the implant and/or the corneal tissue with a laser treatment, chemical treatment, thermal treatment, plasma treatment, corona treatment, flame treatment, or other treatments to create a thin adhesive layer or a layer with adhesive properties greater than the rest of the implant, or in the case of treating a layer of the cornea, greater than the rest of the cornea.

There is provided in accordance with an embodiment of the present invention a method of improving adhesion of an ocular implant to corneal tissue by forming an implant adhesive layer on the ocular implant, the implant adhesive layer having greater adhesive strength than a rest of the implant or by forming a corneal adhesive layer on a posterior surface of a posterior portion of the corneal tissue, the corneal adhesive layer having greater adhesive strength than the rest of the corneal tissue.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
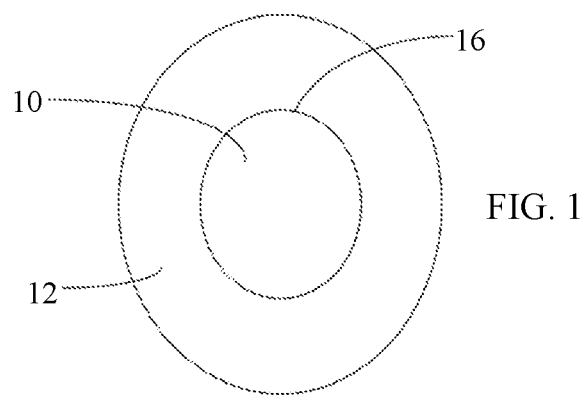
FIGS. 1 and 2 are simplified illustrations, respectively in coronal and transverse planes, of a corneal implant, constructed and operative in accordance with an embodiment of the present invention.
Figure 2:
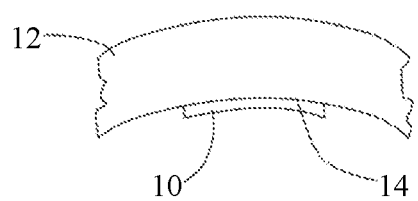

Reference is now made to FIGS. 1 and 2, which illustrate a corneal implant 10, constructed and operative in accordance with an embodiment of the present invention. The implant 10 may be a hydrophobic pseudo-endothelial implant, which can be used instead of an implant from a donor in a DSEK (Descemet Stripping Endothelial Keratoplasty) or DMEK (Descemet Membrane Endothelial Keratoplasty) surgery. Implant 10 serves as a water barrier enabling the dehydration of the cornea.

Implant 10 may be constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as PolyHEMA), polysulfones, thermolabile materials and other relatively hard or relatively soft and flexible biologically inert optical materials, or any combination of such materials, such as a gel encapsulated in a polymer. Implant 10 may thus be rigid, semi-rigid or foldable, for example.

Figures 3A, 3B:
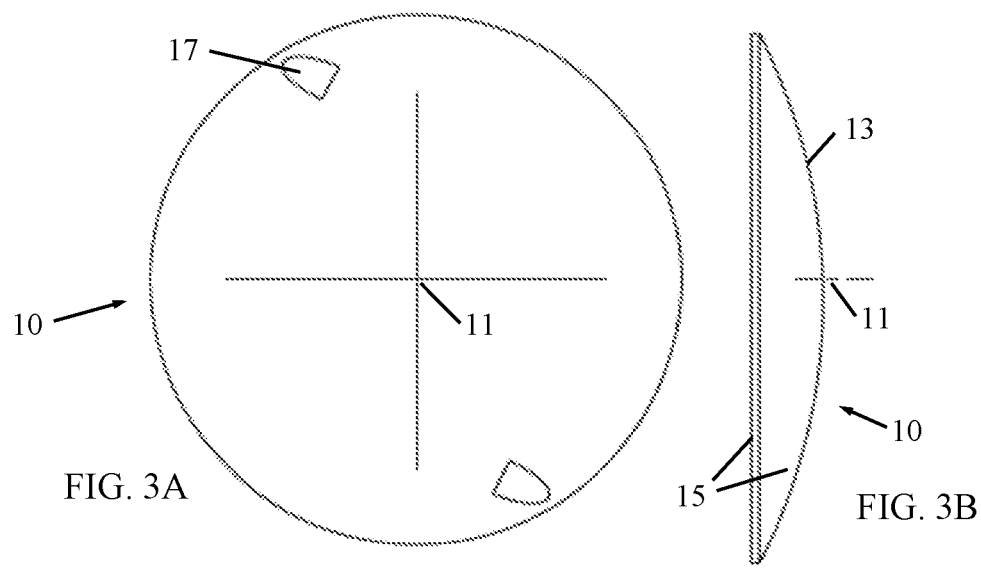
FIGS. 3A and 3B are simplified anterior and side view illustrations of the corneal implant.

As seen in FIGS. 3A and 3B, the corneal implant 10 is dome-shaped with an anterior surface 13 and a posterior surface 15 (anterior and posterior defined to correspond to the anterior-posterior axis 11 of the eye). Pockets, depressions or protrusions 17 may be formed on anterior surface 13 or posterior surface 15 to assist in proper positioning of the implant 10.

Prior to bonding implant 10 to the posterior portion of the cornea, as in PLK (posterior lamellar keratoplasty) or DSEK, a thin posterior or lenticule of stromal tissue (along with Descemet's membrane and endothelial cells attached) may be removed from the cornea of the patient's eye. Alternatively, as in Descemet's strip endokeratoplasty, only the Descemet's membrane and endothelial cells are removed. Alternatively, the implant may be attached to the endothelium of the cornea without any posterior surface striping.

In one embodiment, implant 10 is bonded to the posterior portion of the cornea 12 by means of an implant adhesive layer 14 formed on the anterior surface of implant 10. In another embodiment, implant 10 is bonded to the posterior portion of the cornea 12 by means of a corneal adhesive layer 16 formed on the posterior surface of the posterior portion of the cornea 12. In yet another embodiment, implant 10 is bonded to the posterior portion of the cornea 12 by means of adhesive layer 14 formed on the anterior surface of implant 10 and by means of adhesive layer 16 formed on the posterior surface of the posterior portion of the cornea 12.

Without being bound to any particular theory, adhesion is the tendency of dissimilar surfaces to stick to one another. Adhesion is either measured in terms of work of adhesion ($J/m^2$), which is the energy required to separate 1 square meter of joined materials, or it can be measured as peel force (N/m), which is the force required to pull off a strip of material that is 1 meter wide. It is noted that the work of adhesion is independent of and not proportional to the surface tension. Surface tension plays only a minor role in the adhesion of the two joined materials, but surface tension and wetting may be important for initiating adhesion.

There are different adhesive forces:

1. Mechanical adhesion: the adhesive flows into openings or pores of the substrate and interlocks with the microporosity of the substrate.

2. Electrostatic adhesion: an electrical double layer is formed when two materials come in contact and exchange electrons. This creates an attractive electrostatic or Coulomb force between the two materials.

3. Specific adhesion: atoms/molecules of two adhering surfaces form specific bonds such as hydrogen bonds.

4. Chemical adhesion: atoms/molecules of two adhering materials form chemical bonds that can be of ionic or covalent character.

Adhesive layer 14 may be created by making chemical and/or physical changes on the anterior surface of implant 10 that make the layer 14 more adhesive than the rest of implant 10, such as by creating electrostatic, specific or chemical adhesion between the adhesive layer 14 and the corneal tissue. Similarly, adhesive layer 16 may be created by making chemical and/or physical changes on the posterior surface of the posterior portion of the cornea 12 that make the layer 16 more adhesive than the rest of cornea 12, such as by creating electrostatic, specific or chemical adhesion between the adhesive layer 16 and the implant 10.

For example, by application of laser energy or by applying chemicals or heat treatment on the anterior surface of implant 10 may create chemical changes in the polymer of the implant 10 (e.g., creating covalent bonds) which increase the adhesion of layer 14. As another example, making chemical and/or physical changes on the posterior surface of the posterior portion of the cornea 12 with a femtosecond laser (e.g., passively mode-locked solid state bulk lasers, diode-pumped lasers, titanium sapphire lasers, ultrafast fiber lasers and others) Nd:YAG (neodymium-doped yttrium aluminum garnet) laser, Yb:KGW (ytterbium-doped potassium gadolinium tungstate) laser or Yb:KYW (ytterbium-doped potassium yttrium tungstate) laser and other lasers (pulsed or continuous) that make the layer 16 more adhesive than the rest of cornea 12.

Plasma treatment may be used to increase the adhesion of the implant by creating adhesive layer 14. In plasma treatment, high voltage discharges are created in an air gap, causing free electrons, which are always present in the air, to accelerate and ionize the gases in the air gap. When the electric discharge is very strong, collisions of high velocity electrons with molecules of gas result in no loss in momentum, and electron avalanching occurs. When the implant 10 (made of a plastic, for example, PMMA) is placed in the discharge path, the electrons generated in the discharge impact the surface of the implant with energies that break the molecular bonds on the impact surface (which becomes layer 14). This impact creates very reactive free radicals, which in the presence of oxygen, can react rapidly to form various chemical functional groups on the surface of the implant (layer 14) that increase surface energy and adhesive capability.

Corona treatment may be used to increase the adhesion of the implant by creating adhesive layer 14. During corona discharge treatment, electrons are accelerated into the surface of the implant causing long chains to rupture, producing a multiplicity of open ends and free valences are formed, which increases surface energy and adhesive capability. The corona only changes the top molecule chains, which is 0.00001 micron thick.

Flame treatment may be used to increase the adhesion of the implant by creating adhesive layer 14. By rapidly applying intense heat to the surface of implant 10, molecular chains are broken and polar functional groups are added. Flame treatment also burns off dust, fibers, oils, and other surface contaminates.

The increase adhesion of layer 14 and/or 16 helps create a bond between the implant and the corneal tissue without the need for application of an external adhesive substance.

The following table presents a list of possible treatments for creating the adhesive layer to bond the implant 10 to the posterior portion of the cornea 12. Some of the treatments are listed in the table as being used with an added adhesive material, but it is contemplated that adhesion may be enhance even without the added adhesive material.

| TREATMENT | MATERIAL |
| --- | --- |
| PLASMA (AIR) | — |
| PLASMA (O$_2$) | NIPAM (N-isopropylacrylamide) |
|  | Allylamine |
|  | Allyl alcohol |
|  | Acrylic Acid |
| PLASMA (O$_2$/CO$_2$) | EDC + Collagen |
|  | EDC + Polylisinc + star-PEG |
| PLASMA (AR + O2) | Vinyl alcohol |
|  | pp-HMDSO |
| E-BEAM | NIPAM |
| UV POLYMERIZATION | NIPAM |
|  | Polyglycidyl ether |
| LASER | — |
| ATOMIC DIFFUSION BONDING | — |
| SPIN COATING | NIPAM |
| — | Cyanoacrylate |
| — | Amino acid DOPA |
| FREE RADICAL POLYMERIZATION | NIPAM |

What is claimed is:

1. A method for preparing an implant for attachment to a posterior surface of the cornea, comprising:
   providing a corneal copolymer implant comprising the monomer 2-hydroxyethyl methacrylate and having an anterior surface and a posterior surface, and
   exposing at least the anterior surface of the implant to a treatment that improves adhesion between the implant and the cornea.

2. The method of claim 1 wherein the implant comprises a barrier to water.

3. The method of claim 1 wherein the implant has a dome shape.

4. The method of claim 1 wherein the treatment is a member selected from the group consisting of application of chemicals, heat, laser energy, flame, plasma and electric discharge.

5. The method of claim 4 which comprises applying laser energy from a Nd:YAG laser.

6. The method of claim 4 which comprises applying laser energy from a Yb:YAG laser.

7. The method of claim 1 wherein the treatment forms an adhesive layer on the anterior surface of the implant.

8. The method of claim 1 wherein the treatment comprises applying plasma and oxygen to at least the anterior surface of the implant.

9. The method of claim 1 wherein the implant comprises a member selected from the group consisting of hyaluronic acid, and the potassium and sodium salts thereof.

10. The method of claim 1 wherein the implant comprises pockets, depressions or protrusions on the anterior surface or the posterior surface.

11. A method for making an ocular implant which comprises providing a dome-shaped implant comprising PMMA or Poly HEMA and applying laser energy to at least an anterior surface of said implant to configured said implant for attachment to a posterior surface of the cornea, said anterior surface being an adhesive surface for attaching the implant to the posterior surface of the cornea.

12. A method for making an ocular implant which comprises providing a transparent dome-shaped implant having an anterior surface and a posterior surface, the implant comprising PMMA or Poly HEMA and treating at least one surface of the implant to improve adhesion between the implant and a posterior surface of a cornea.

13. The method of claim 12 wherein the treatment is a member selected from the group consisting of application of chemicals, heat, laser energy, flame, plasma and electric discharge.

14. The method of claim 13 wherein the treatment comprises application of laser energy to the implant.

15. The method of claim 13 wherein the treatment comprises application of chemicals to the implant.

16. The method of claim 14 which comprises applying laser energy to the anterior surface of the implant.

17. The method of claim 12 wherein the at least one surface is the anterior surface.

18. The method of claim 17, wherein the treating step comprises a physical treatment of the anterior surface.

19. A method comprising:
improving adhesion of an external surface of an ocular implant which is made of a polymeric material by making a change to said external surface that changes a chemical feature of said polymeric material which improves adhesion of said external surface to a posterior surface of a cornea.

20. The method of claim 19, wherein said change to said external surface comprises creation of hydrogen bonds.

21. The method of claim 19, wherein said polymeric material comprises a partially hydrolyzed polymeric material.

22. The method of claim 19, wherein said polymeric material comprises a methacrylic polymer.

23. The method of claim 19, wherein said polymeric material comprises a hydroxyethyl methacrylate.

24. The method of claim 19, wherein said polymeric material comprises a methylmethacrylate.

25. The method of claim 19, further comprising implanting said ocular implant against a posterior surface of a cornea, wherein said external surface adheres to the posterior surface of the cornea.

26. The method of claim 25, further comprising using said ocular implant as a water barrier to treat corneal edema.

* * * * *